United States Patent [19]
Wagner

[11] 3,971,374
[45] July 27, 1976

[54] SYMMETRIC PADDED BANDAGE FOR INJURED PALM OF EITHER HAND

[76] Inventor: William H. Wagner, 5405 W. Eva St., Glendale, Ariz. 85301

[22] Filed: May 5, 1975

[21] Appl. No.: 574,683

[52] U.S. Cl. .............................................. 128/155
[51] Int. Cl.² ......................................... A61F 13/00
[58] Field of Search ................... 128/165, 155–157, 128/149, 77, 154

[56] References Cited
UNITED STATES PATENTS

| | | | |
|---|---|---|---|
| 432,798 | 7/1890 | Hirst | 128/154 X |
| 3,234,941 | 2/1966 | Tucker | 128/154 |
| 3,297,028 | 1/1967 | Murray | 128/157 |

Primary Examiner—Lawrence W. Trapp
Attorney, Agent, or Firm—Edwin M. Thomas

[57] ABSTRACT

A bandage for protecting an injury to the palm of the hand, especially the concave part of the palm, comprises an outer adhesively coated sheet having a central area to which a gauze pad is affixed to cover the wound, and symmetrically arranged branches, also adhesively coated, for securing the bandage in place securely in a manner to permit maximum use of the hand while making sure the pad stays in place in the hollow of the palm. Radially extending arms, symmetrically arranged, are provided respectively to attach to the base of the hand or wrist and to extend between the third and fourth fingers; other arms or branches extend around the base of the thumb and around the opposite side of the hand, still others are selectively attachable to index or little fingers (depending on which hand, right or left, is being bandaged) and further arms are designed to wrap around either between thumb and forefinger or around the hand under or near the little finger knuckle. Supplemental padding may be added for a deeply concave palm or for thicker pad protection, when needed.

6 Claims, 5 Drawing Figures

U.S. Patent  July 27, 1976  3,971,374
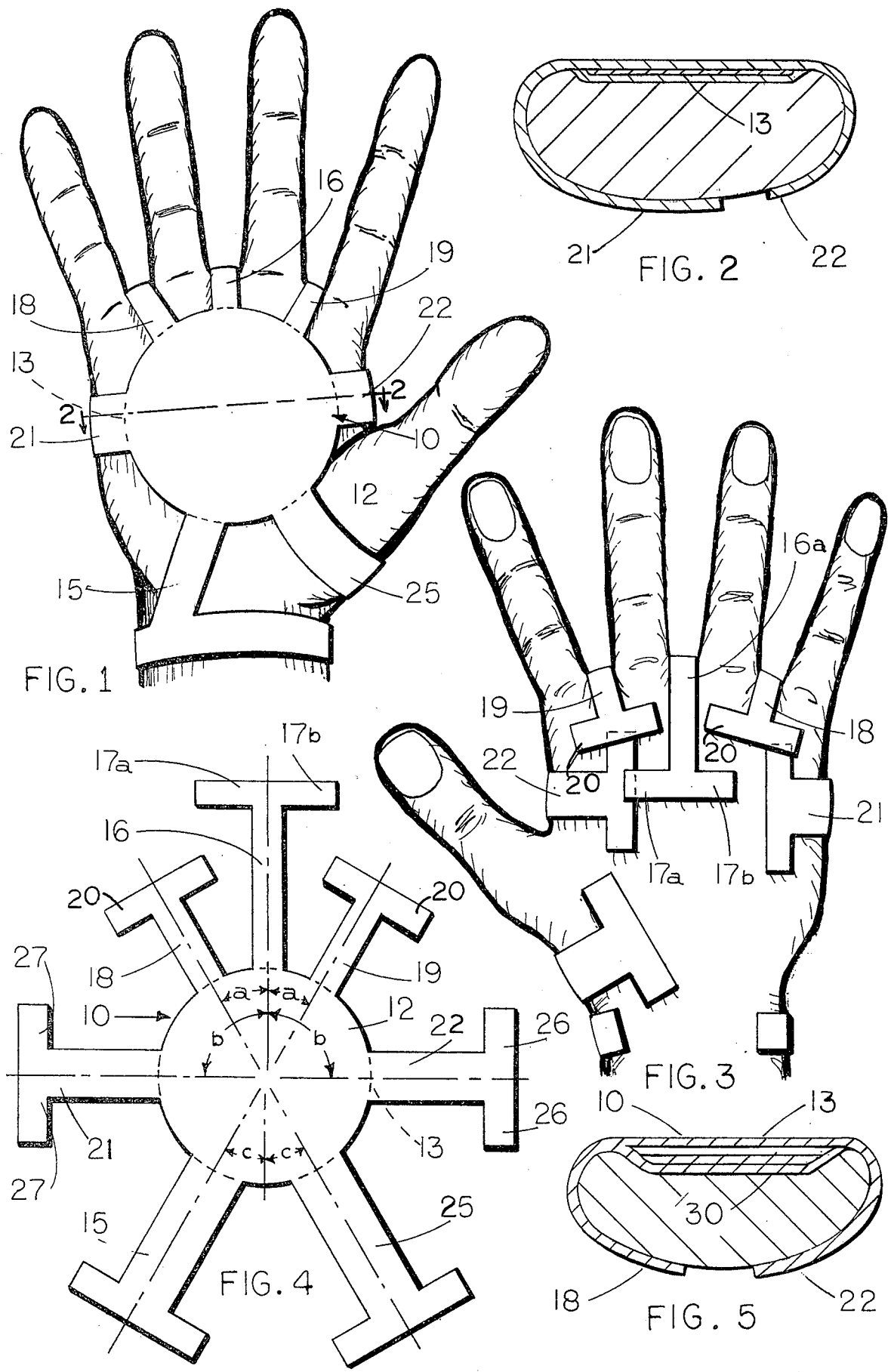

SYMMETRIC PADDED BANDAGE FOR INJURED PALM OF EITHER HAND

BACKGROUND AND PRIOR ART

An object of the present invention is to provide a versatile bandage, applicable to either a right or a left hand, to give protection to an injury to the palm, such as a cut or deep burn, in a manner to permit reasonable use of the injured hand.

Bandages of many kinds are available for many different parts of the human body, for covering and protecting cuts, burns and other injuries. Available devices include the widely used strip bandages, consisting simply of an adhesively coated strip which bears a small pad of protective material, such as several layers of surgical gauze which may or may not be impregnated with medicinal materials. In addition to these, finger stalls and other specially designed bandages are available for fingers or toes. Paddings of special shapes and securing devices of numerous kinds are obtainable and many of these are widely used. However, as far as applicant is aware, none or these is suitable for the specific purpose of wrapping and protecting an injured hand palm, especially the concave part of the palm. Because of its shape, the concave palm is difficult to bandage. In many cases, the whole hand is wrapped massively, converting it temporarily into a sort of stump, which virtually makes it useless until the bandage can be removed. In some cases, of course, such wrapping or casting may be necessary but more often it is done because there is no handy, effective bandage available which will cover the palm and give it the needed protection.

In U.S. Pat. No. 2,095,603 there are described combinations of stalls and splints for protecting an injured hand. These are not intended for or suitable for the palm of the hand. Similarly, in U.S. Pat. No. 2,561,863, a glove type wrapper or bandage having finger elements is described which might be useful for certain injuries but not for the palm of the hand. Several other patents show glove-type wrappers, such as U.S. Pat. Nos. 2,074,762 and 3,084,686. The latter is indicated as being useful also for wrapping a foot, but it does not appear to be suitable for use on an injured concave-shaped palm. U.S. Pat. No. 2,658,510 shows a foot bandage said to be useful also on hands but it again is not suitable for the purposes of the present invention. The glove type devices obviously are made in right and left hand forms, and their use, even if they were otherwise suitable, would necessitate stocking both right and left gloves, with added inventory and expense to the user or supplier.

Some general type bandages having radially or other extending arms are shown in such references as U.S. Pat. Nos. 3,297,028 and 3,520,306. While doubtless useful for other purposes these devices again are not satisfactory for protecting the injured palm of a hand because of its peculiar concave shape and the difficulty of keeping the bandage properly in place, or keeping the padding properly in place, once the bandage has been applied to the area. In particular, the prior art devices are not designed to allow the patient to use his injured hand. Many and probably most hand injuries are not completely disabling and it is desirable to permit the injured person to continue to do what work he can. If the hand is so extensively wrapped as to make it useless, this is often an unnecessary handicap.

A particular object of this invention, then, is to make available a versatile bandage which can be applied to either hand, which will stay in place, and which will give maximum freedom, so far as use of the thumb and fingers is concerned, while protecting well the concave hollow palm where the injury is. To do this in a way that makes the bandage applicable equally well to either the right or the left hand, with securing elements located so as to give the necessary holding ability, is a further object.

The invention will be understood more fully by reference to detailed description of a preferred embodiment which follows:

BRIEF DESCRIPTION OF DRAWINGS

FIG. 1 is a front view of a right hand to which the bandage of the present invention is secured.

FIG. 2 is a sectional view showing padding, taken substantially along line 2—2 of FIG. 1.

FIG. 3 shows the back side of the hand with bandage attached as in FIG. 1.

FIG. 4 is a plan view of the bandage.

FIG. 5 is a sectional view similar to FIG. 2 of a modification of the bandage, showing it attached to a hand.

DESCRIPTION OF PREFERRED EMBODIMENT

Referring now to the drawings, FIG. 4 shows the bandage before application and the other figures show it attached to a human hand. FIG. 1, in particular, shows the bandage as comprising an adhesively coated sheet, the adhesive coating preferably being of the conventional pressure-sensitive type, and it may be covered with a strippable film or sheet to protect the adhesive and keep it sanitary until time for use. This sheet 10 has a central area 12 shown as being substantially circular in shape, which is adapted to overlie the concave or hollow part of the hand. Secured adhesively to sheet 10 or in any other manner that is suitable, is a gauze pad 13, FIG. 2, which may be made up of several layers of surgical gauze or other suitable and antiseptic padding material. It is shown as being circular in shape and as coinciding in area with the circular area 12, but it may be larger or smaller in area, if desired, depending on the type of injuries for which it may be designed.

Extending more or less radially outward from the circular area 12 are a number of arms or branches of the same material 10, arranged symmetrically in pairs. The reason for the symmetric arrangement, as will be more fully explained, is to have the securing tabs or branches positioned so that they may be fastened to appropriate parts of either a right or a left hand. At the bottom, as seen in FIG. 1, a tab or arm 15 is adapted to be fastened to the heel of the hand; it is preferably long enough to extend onto the wrist. Opposite, at the top as seen in FIG. 1, a vertically extending tab 16 is adapted to be passed between the third and fourth fingers of either a right or a left hand and folded down onto a fastened to the back of the hand. This turned down part 16a is shown in FIG. 3. It may have side arms 17a and 17b to left and right.

Similarly, at upper right and left, a symmetrical pair of tabs or arms 18 and 19 are adapted, respectively, to be passed between the middle finger and an adjacent finger to the right or to the left. In FIG. 3, the member 18 is shown passing between the fourth finger and the little finger of a right hand. Member 19 passes between the index finger and the third finger of a right hand but if this were a left hand instead of a right, their functions would be reversed, as is obvious.

Projecting leftward and rightward, as seen in FIG. 1, are another pair of arms or tabs 21 and 22. As shown in FIGS. 1 and 3, these are adapted, respectively, to be secured to the left edge and back of a right hand below the little finger, and to the back of the hand between index finger and thumb. Conversely for a left hand.

The tab 15, shown extending on the wrist, FIG. 1, is matched by a similar and symmetrical tab 25 which passes around the base of a right hand, below the thumb. On a left hand, tab 25 would fasten to the wrist as does tab 15 in FIG. 1.

For hands of different sizes, the bandage can be placed higher or lower than shown in FIG. 1; its position is determined largely but not entirely by tabs 16, 18 and 19 which pass between fingers as just described. The other tabs at right and left are not so critically positioned and can be fastened higher than shown. As seen in FIG. 3, the tabs 18 and 19 are provided with lateral extensions 20. These tabs can be inverted 180° and wrapped around the index and little fingers, if desired. Similarly, tabs 21 and 22 have lateral extensions 26 and 27, respectively. The symmetrical arrangement of tabs in pairs, such as 18, 19 and 21, 22, facilitate application to either hand. In fact, the bandage can be used also on the back of a hand, if needed.

For small children, the bandage may be produced in one or more small sizes; for adults and most adolescents, a single size will often suffice, making it unnecessary to stock a large variety of sizes. However, several sizes may be produced if needed.

The arrangement of the pad 13 is such that it is held snugly against the palm of the hand, even when the hand is closed or partly closed, the pad being thick enough to fill the usual concavity or "hollow" of the hand. Since some hands are more cupped than others, having a deeper hollow, it may be desirable in some cases to add supplemental padding. FIG. 5 shows an extra thick padding arrangement, comprising the main gauze pad 13 and supplemental pad or pads 30. In all cases, the arrangement of the fastening tabs is such that the pad is held under soft pressure against the palm, protecting the injury from entrance of dirt under the bandage.

In FIG. 4 the angular arrangements of the various tabs are shown. Taking the center line of the wrist between tab 15 and tab 25, and the upper tab 16 as the axis of symmetry, the axes of the tabs 18 and 19 lie at an angle $a$ to left and right respectively of the first axis. Angle $a$ may be varied somewhat but is preferably between about 25° and 35°, e.g., about 30° from the axis. The tabs 21 and 22 are formed at angles $b$ with respect to the same axis, preferred values being about 80° to 100°, e.g., about 90°. Tabs 15 and 25 are formed at angles $c$ with respect to the axis of symmetry, having a value of about 25° to 40°, a 30° angle being appropriate in most cases.

While the arrangement shown is presently preferred, it will be obvious that more or fewer tabs may be used and their arrangement may be varied somewhat, but they should be sufficient in number and spaced in such a manner that they will hold the bandage securely in place, whether the hand is open flat or partly or entirely closed. The finger separating tabs 18 and 19 are so located that they are selectively and interchangeably suited for fitting between the index finger or the little finger and the next finger adjacent, depending whether the hand to be bandaged is a right or a left hand. The other tabs sometimes can be located with less precision, as long as they permit placing the bandage on either a left hand or a right hand without undue interference with the action of the thumb.

It will be obvious that the modifications suggested above and others which may occur to those skilled in the art may be made without departing from the spirit and purpose of the invention. It is intended by the claims which follow to cover such obvious changes and variations and their equivalents as broadly as the state of the prior art properly permits.

What is claimed is:

1. A bandage suitable for protecting an injured palm of either a right or a left hand which comprises a sheet of wrapping material coated adhesively on its inner surface for adhesion to the skin and comprising a central area to cover the hollow part of the hand and plural pairs of tabs extending more or less radially from said central area, each pair of said tabs being arranged substantially symmetrically with respect to an axis aligned along the wrist and between the third and fourth fingers, one pair of said tabs being positioned to engage respectively the little finger and the index finger of a right hand or alternatively the index finger and little finger of a left hand, and a protective pad secured to the sheet in position to cover and protect said injured palm, the tabs being sufficient in number and so arranged as to hold said pad against said palm in either open or relatively closed conditions of the hand.

2. A bandage according to claim 1 which includes a pair of opposed tabs extending along said axis for securing respectively to the base of the hand or wrist and between the third and fourth fingers of either a right or a left hand.

3. A bandage according to claim 2 which also includes opposed pairs of tabs extending to right and left of said axis for attachment respectively to the little finger side of a right hand and above and below the thumb or alternatively for attachment to a left hand.

4. A bandage according to claim 2 which includes a supplemental pad for filling a deeply cupped hand so as to be held under compression in all conditions, open or closed, of said hand.

5. A bandage according to claim 1 which includes a supplemental pad for a deeply cupped hand.

6. A bandage according to claim 1 which includes a wrist-engaging tab extending substantially along said axis, an opposite tab for engagement between the third and fourth fingers also extending along said axis, a pair of opposite and symmetrically disposed tabs adapted to engage respectively between the thumb and forefinger of a right hand and around the base of the little finger of a right hand or in reverse order when applied to a left hand, and an additional pair of tabs also symmetrically disposed with respect to said axis for engaging the base of the thumb and around the base of the hand opposite the thumb for further securing said bandage in position.

* * * * *